United States Patent [19]

Quann

[11] Patent Number: 4,665,245

[45] Date of Patent: May 12, 1987

[54] PROCESS FOR PREPARING ALPHA-OLEFINS FROM LIGHT OLEFINS

[75] Inventor: Richard J. Quann, Moorestown, N.J.

[73] Assignee: Mobil Oil Corporation, New York, N.Y.

[21] Appl. No.: 816,072

[22] Filed: Jan. 3, 1986

[51] Int. Cl.⁴ .......................... C07C 2/12; C07C 6/02
[52] U.S. Cl. .................................... 585/316; 585/315; 585/329; 585/533; 585/646; 585/647; 585/415
[58] Field of Search .............. 585/315, 316, 329, 533, 585/646, 647, 510, 415

[56] References Cited

U.S. PATENT DOCUMENTS

| | | | |
|---|---|---|---|
| 3,590,094 | 6/1971 | Reusser et al. | 585/316 |
| 3,647,906 | 3/1972 | Farley | 585/316 |
| 3,660,516 | 5/1972 | Crain et al. | 585/316 |
| 3,883,606 | 5/1975 | Banks | 585/646 |
| 3,915,897 | 10/1975 | Reusser et al. | 502/241 |
| 3,952,070 | 4/1976 | Nowak et al. | 585/646 |
| 4,180,524 | 12/1979 | Reusser et al. | 585/646 |
| 4,409,409 | 10/1983 | Langer et al. | 585/524 |
| 4,431,855 | 2/1984 | Reusser et al. | 585/646 |
| 4,499,328 | 2/1985 | Kukes et al. | 585/646 |
| 4,504,694 | 3/1985 | Kukes et al. | 585/646 |
| 4,517,396 | 5/1985 | Hoek et al. | 585/415 |
| 4,517,399 | 5/1985 | Chester et al. | 585/533 |
| 4,517,401 | 5/1985 | Kukes et al. | 585/646 |
| 4,524,232 | 6/1985 | Chester et al. | 585/533 |
| 4,547,612 | 10/1985 | Tabak | 585/533 |
| 4,547,617 | 10/1985 | Welch | 585/646 |

OTHER PUBLICATIONS

Olefin Metatheis: Technology and Application, *Applied Industrial Catalysis*, vol. 3, Chap. 7, pp. 215 et seq.

*Primary Examiner*—Asok Pal
*Attorney, Agent, or Firm*—Alexander J. McKillop; Michael G. Gilman; L. G. Wise

[57] ABSTRACT

A process for preparing alpha-olefins is provided which comprises:

(a) converting a feed containing one or more lower olefins in the presence of a medium pore crystalline silicate zeolite catalyst under reaction conditions providing a mixture of higher olefinic products;

(b) contacting at least a part of the mixture of higher olefinic products resulting from step (a) with an alpha-olefin in the presence of a metathesis catalyst under olefin metathesis conditions to provide a mixture of alpha-olefins having a different carbon number than the feed olefin;

(c) separating the alpha-olefin product of step (b) into at least two fractions, one fraction containing predominantly lower alpha-olefin hydrocarbons and the other fraction containing predominantly higher alpha-olefin hydrocarbons; and, (d) recycling at least a part of the lower alpha-olefin hydrocarbon fraction resulting from step (c) as feed for step (a).

18 Claims, 1 Drawing Figure

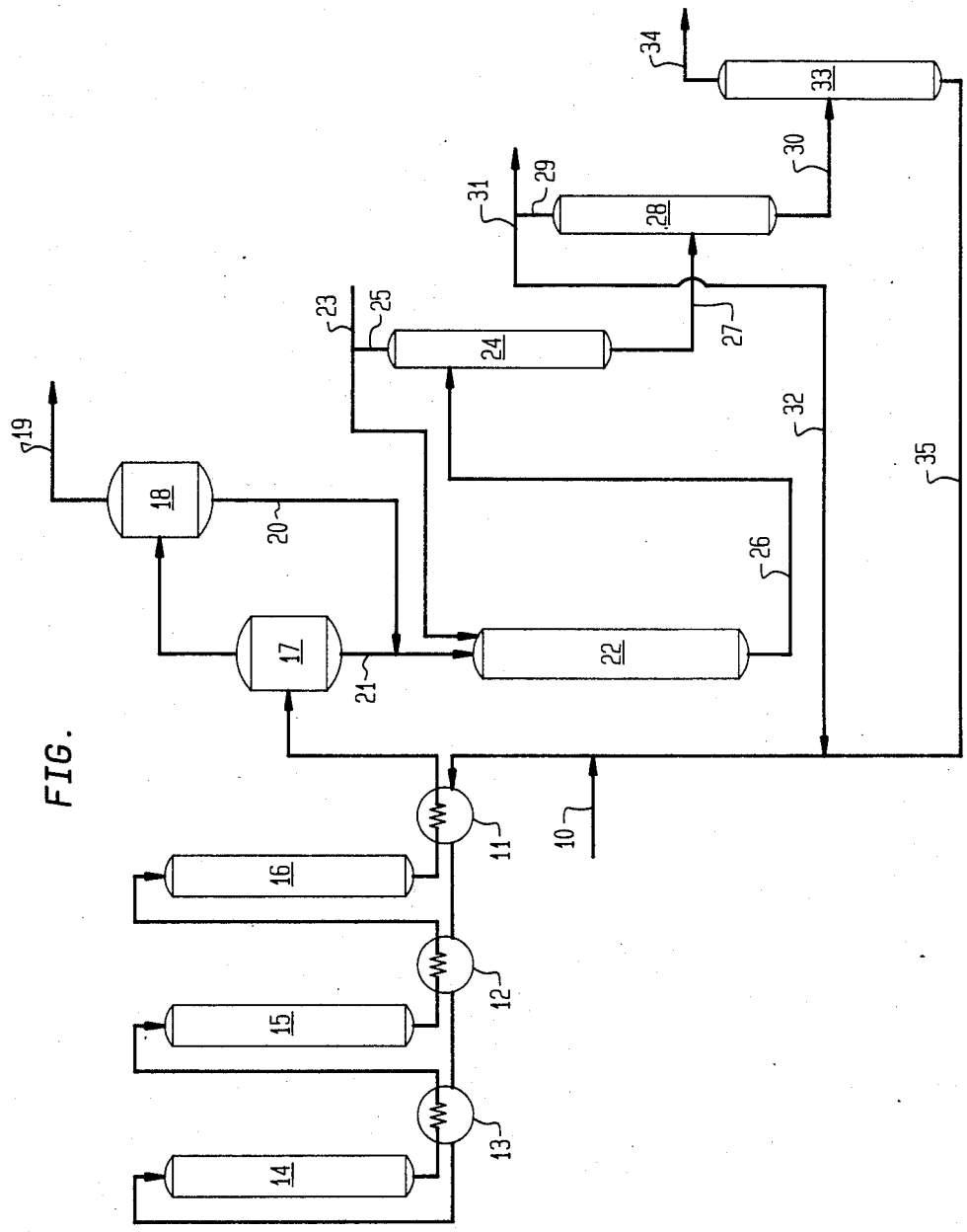

PROCESS FOR PREPARING ALPHA-OLEFINS FROM LIGHT OLEFINS

BACKGROUND OF THE INVENTION

This invention relates to a multi-stage process for preparing alpha-olefins from light olefins. In an initial stage, light olefins such as propylene, butylene, and the like, are converted in the presence of a shape selective crystalline zeolite catalyst to higher olefins. At least a portion of these higher olefins are then reacted with alpha-olefin in the presence of a metathesis (disproportionation) catalyst to provide alpha-olefins having different numbers of carbon atoms than that of the feed olefins. The alpha-olefin product resulting from the metathesis operation is further processed to provide at least two fractions the lighter of which is recycled as cofeed to the first stage conversion unit.

Conversion of olefins to gasoline and/or distillate products is disclosed in U.S. Pat. Nos. 3,960,978 and 4,021,502 wherein gaseous olefins in the range of ethylene to pentene, either alone or in admixture with paraffins, are converted into an olefinic gasoline blending stock by contacting the olefins with a catalyst bed made up of ZSM-5 zeolite. In U.S. Pat. No. 4,227,992, the operating conditions for the selective conversion of $C_3+$ olefins to mainly aliphatic hydrocarbons in the gasoline/distillate range is disclosed. In a related manner, U.S. Pat. Nos. 4,150,062 and 4,211,640 disclose a process for converting olefins to gasoline components.

In the process for catalytic conversion of olefins to heavier hydrocarbons by catalytic oligomerization using a medium pore shape selective acid crystalline zeolite, such as ZSM-5 catalyst, process conditions can be varied to favor the formation of hydrocarbons of varying molecular weight. At moderate temperature and relatively high pressure, the conversion conditions favor $C_{10}+$ aliphatic product. Lower olefinic feedstocks containing $C_2$-$C_8$ alkenes may be converted; however, the distillate mode conditions does not convert a major fraction of ethylene. U.S. Pat. No. 4,547,612 discloses a continuous process for the catalytic conversion of olefins to lubricant or heavy distillate range compounds in which a light olefin feedstock, e.g., propylene, is combined with a $C_5+$ olefin stream recovered from previous product effluent.

Olefin metathesis (disproportionation) is a known type of reaction in which one or more olefinic compounds are transformed into other olefins of different molecular weights. The reaction of an olefin with itself to produce an olefin of a higher molecular weight and an olefin of a lower molecular weight can also be referred to as a self-disproportionation. For example, propylene can be disproportionated to ethylene and cis-, and trans-2-butene. Another type of disproportionation involves the cross-disproportionation of two different olefins to form still other olefins. An example would be the reaction of one molecule of 2-butene with one molecule of 3-hexene to produce two molecules of 2-pentene. Another example of a cross-disproportionation involves the reaction of an internally unsaturated olefin with an alpha-olefin to provide two different alpha-olefins, e.g., the reaction of 2,4,4-trimethyl-2-pentene with ethylene to provide equimolar amounts of 3,3-dimethyl-1-butene (neohexene) and isobutene as shown in Banks, "Olefin Metathesis: Technology and Application", *Applied Industrial Catalysis,* Vol. 3, Chapter 7, pp. 215 et seq., Leach, ed. (1984).

Among the catalysts that have been developed for olefin metathesis are those comprising inorganic refractory materials containing a catalytic amount of at least one of molybdenum oxide and tungsten oxide. Other olefin metathesis reactions and catalyst compositions therefor are described in U.S. Pat. Nos. 3,883,606; 3,915,897; 3,952,070; 4,180,524; 4,431,855; 4,499,328; 4,504,694; 4,517,401; and, 4,547,617, among others.

The terms "disproportionation" and "metathesis" as used herein mean the conversion of an olefinic hydrocarbon feed to a mixture of product olefinic hydrocarbons having different numbers of carbon atoms than the feed olefins.

SUMMARY OF THE INVENTION

In accordance with the present invention, a process for preparing alpha-olefins is provided which comprises:

(a) converting a feed containing one or more lower olefins in the presence of a medium pore crystalline silicate zeolite catalyst under reaction conditions providing a mixture of higher olefinic products;

(b) contacting at least a part of the mixture of higher olefinic products resulting from step (a) with an alpha-olefin in the presence of a metathesis catalyst under olefin metathesis conditions to provide a mixture of alpha-olefins having a different carbon number than the feed olefin;

(c) separating the alpha-olefin product of step (b) into at least two fractions, one fraction containing predominantly lower alpha-olefin hydrocarbons and the other fraction containing predominantly higher alpha-olefin hydrocarbons; and, (d) recycling at least a part of the lower alpha-olefin hydrocarbon fraction resulting from step (c) as feed for step (a).

At steady state operation, the aforedescribed process can be thought of as a continuous procedure for converting light olefin to higher molecular weight, slightly branched alpha-olefins. The boiling range of the desired product alpha-olefins can be relatively narrow or broad as desired, the overall conversion still remaining one of a light alpha-olefin or mixture of light alpha-olefins to more valuable heavier alpha-olefins. The product alpha-olefins herein are useful as basestocks for lube preparation or as feedstocks for the manufacture of a variety of industrial and commercial materials such as solvents, acids, detergents, etc., with little if any undesirable or lesser value by-products. Thus, the lower molecular weight alpha-olefins which are a necessary consequence of the combined reaction system can be constantly recycled so that the net result of the process is the production of the more desirable higher molecular weight alpha-olefins.

BRIEF DESCRIPTION OF THE DRAWING

The accompanying drawing is a schematic representation of one embodiment of the process of the invention showing process flow streams and unit operations.

DESCRIPTION OF THE PREFERRED EMBODIMENTS

The first stage conversion of light olefin to higher olefin can take place in a single reactor or a series of reactors. In the case of the latter, each reactor can be packed with the same or a different zeolite catalyst.

Essentially any of the known zeolite-catalyzed olefin oligomerization processes can be employed in carrying out the first stage of the process herein.

The shape-selective oligomerization/polymerization catalysts preferred for use in the oligomerization stage of the process herein include the crystalline aluminosilicate zeolites having a silica to alumina molar ratio of at least 12, a constraint index of from about 1 to about 12 and acid cracking activity of about 50–300. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable shape selective medium pore catalyst for fixed bed use is a small crystal HZSM-5 zeolite (silica:alumina ratio=70:1) with alumina binder in the form of cylindrical extrudates of about 1–5 mm. Unless otherwise stated in this description, the catalyst shall consist essentially of ZSM-5 which has a crystallite size of about 0.02 to 0.05 micron. Other pentasil catalysts which can be used in one or more reactor stages include a variety of medium pore (about 5 to 9 angstroms) siliceous materials such as borosilicates, ferrosilicates, and/or aluminosilicates such as are disclosed in U.S. Pat. Nos. 4,414,423 and 4,417,088, both of which are incorporated herein by reference.

The surface activity of these catalysts can be modified by pretreatment, e.g., with a surface-neutralizing base as disclosed in U.S. Pat. No. 4,520,221.

Shape-selective oligomerization as it applies to the conversion of $C_2$–$C_{10}$ olefins over ZSM-5 is known to produce higher olefins of up to $C_{30}$ and even higher. As reported by Garwood in "Conversion of $C_{2-10}$ to Higher Olefins over Synthetic Zeolite ZSM-5," ACS SVmPosium Series, No. 218, Intrazeolite Chemistry (American Chemical Society 1983), reaction conditions favoring higher molecular weight product are low temperature (200°–260° C.), elevated pressure (about 2000 kPa or greater), and long contact time (less than 1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of ZSM-5 type catalysts impose shape-selective constraints on the configuration of the large molecules, accounting for the differences with other catalysts.

The following model reaction path for the oligomerization of propylene is set forth for purposes of explanation, and it should be taken as a theoretical path as the process is presently understood by workers in the field.

$C_3^=$(propylene)oligomerization $\longrightarrow$ $C_6^=$, $C_9^=$, $C_{12}^=$, etc.

($C_3^=$ oligomers);

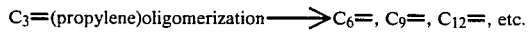

Isomerization and cracking $\longrightarrow$ 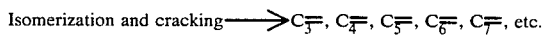

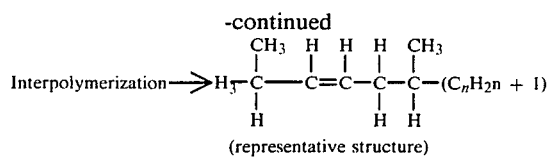

(representative structure)

Typically, employing HZSM-5 catalyst with propylene as feed, a mixture of olefins predominantly made up of long chain materials with limited branching, e.g., methyl, having internal double bonds is obtained.

The final molecular conformation is influenced by the pore structure of the catalyst and the ratio of intracrystalline acid sites to surface acid sites. For the higher carbon numbers, the structure is primarily a methyl-branched, long backbone olefinic chain, with the maximum cross section of the chain limited by the dimension of the largest zeolite pore. Although emphasis is placed on the normal 1-alkenes, particularly, propylene, as feed stocks, other lower olefins such as 2-butene or isobutylene are readily employed as starting materials due to rapid isomerization over the acidic zeolite catalyst. At conditions chosen to maximize heavy distillate and lubricant range products ($C_{20}+$), the raw aliphatic product is essentially mono-olefinic. Overall branching is not extensive, with most branches being methyl at about one branch per eight or more atoms.

It is believed that two modes of oligomerization/polymerization of olefins can take place over acidic zeolites such as HZSM-5. One reaction sequence takes place at Bronsted acid sites inside the channels or pores producing essentially linear materials. The other reaction sequence occurs on the outer surface producing highly branched material. By decreasing the surface acid activity (surface alpha-value of such zeolites, fewer highly branched products with low VI are obtained.

Several techniques can be used to increase the relative ratio of intra-crystalline acid sites to surface active sites. This ratio increases with crystal size due to geometric relationship between volume and superficial surface area. Deposition of carbonaceous materials by coke formation can also shift the effective ratio. However, enhanced effectiveness is observed where the surface acid sites of small crystal zeolites are reacted with a chemisorbed organic base or the like.

Catalysts of low surface activity can be obtained by using medium pore zeolites of small crystal size that have been deactivated by basic compounds, examples of which are amines, phosphines, phenols, polynuclear hydrocarbons, cationic dyes and others. These compounds all must have a minimum cross section diameter of 5 angstroms or greater. Examples of suitable amines include monoamines, diamines, triamines, aliphatic and aromatic cyclic amines and heterocyclic amines, porphines, phthalocyanines, 1,10-phenanthroline, 4,7-diphenyl-1,10-phenanthroline, 3,4,7,8-tetramethyl-1,10-2,4,6-tri(2-pyridyl)-S-triazine and 2,3-cyclododecenopyridine. Examples of phosphines include triphenylphosphine and 1,2-bis(diphenylphosphine)ethane. Suitable metal compounds are magnesium acetate, metal-porphines, such as hemin or iron (III) porphine chloride, cobalticinium chloride $(C_5H_5)_2CoCl$, and titanocene dichloride (biscyclopentadienyl titanium dichloride), large complex cations such as $[Co(NH_2R)_6]^{2+}$, where R=H, alkyl, $[Pt(NH_2R)_4]^{2+}$, where R=alkyl, $[co(en)_3]^{3+}$ where en=ethylene-diamine, manganese (III) meso-tetraphenylporphine.

Alternatively, the catalysts can be treated with organic silicon compounds, as described in U.S. Pat. Nos. 4,100,215 and 4,002,697, to impart the desired degree of surface deactivation while being essentially free of carbonaceous deposits. Such treatment involves contacting the catalyst with a silane surface-modifying agent capable of deactivating catalytic (acidic) sites located on the external surface of the zeolite by chemisorption.

Conventional temperatures, pressure and equipment can be used in the oligomerization operation of the process herein. Preferred temperature can vary from about 100° to about 350° C., preferably from about 150° to about 250° C., with pressures varying from about atmospheric to about 20,000 kPa (3000 psi) and a WHSV of from about 0.01 to about 2.0, preferably 0.2 to 1.0.

The metathesis (disproportionation) conversion of the olefinic hydrocarbons resulting from the olefin oligomerization operation are converted to alpha olefins in a primary reaction which can be thought of as comprising the breaking of two unsaturated bonds between first and second carbon atoms and between third and forth carbon atoms, respectively, and the formation of two new alpha olefinic bonds in different molecules as in the following formulas (illustrating ethylene as the feed alpha-olefin):

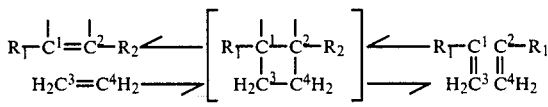

In general any of the $C_{2-8}$ alpha olefins can be reacted with the oligomerization product effluent in the metathesis operation herein. Some specific examples of such alpha-olefins are ethylene, propylene, 1-butene, 1-pentene, 1-hexene, 1-octene, and the like with ethylene being preferred.

Any of the catalysts heretofore employed in olefin metathesis are suitably utilized in the second stage conversion herein. Many of these catalyst have been reported in the prior art. Preferably, the disproportionation catalyst is one of molybdenum, tungsten, or rhenium oxide deposited on a support of silica, alumina, silica-alumina or aluminum phosphate. An additional metal oxide, e.g., a rare earth metal oxide, can also be present as is known. Prior to its use, the catalyst is activated by calcination carried out in a conventional manner. A particularly suitable catalyst is molybdenum oxide supported on a mixture of amorphous precipitated silica and colloidal silica.

Suitable conditions for the metathesis reaction include a pressure of from about 0–5000 psig, a temperature of from about ambient to about 1000° F., and space velocities of from about 1 to about 300 WHSV based on the nature of the metathesis catalyst. Although the activity of the catalyst is suitable within the broad ranges mentioned above, increased activity is generally found when the pressure is from about 100 to about 500 psig, the temperature range is from about 650°–850° F., and the WHSV is from about 0.5 to about 1000. The particular temperature, pressure and flow rates utilized within these ranges is largely dependent on the properties of the feed material undergoing the metathesis conversion. The process can be carried out either in the presence or absence of a diluent. Diluents comprising paraffinic and cycloparaffinic hydrocarbons can be employed. Suitable diluents are, for example, propane, cyclohexanes, methylcyclohexane, normal pentane, normal hexane, isotane, dodecane, and the like, or mixtures thereof, including primarily those paraffins and cycloparaffins having up to 12 carbon atoms per molecule. The diluent should be nonreactive under the conditions of the reaction. In some instances the use of the diluent can increase the selectivity of the conversion to primary products. The reaction can also be carried out in a single unit or a battery of units employing the same or a different catalyst.

The amount of alpha-olefin employed in the metathesis conversion can vary widely and will depend in part on the degree of unsaturation in the higher olefin feed which can be readily quantified employing known techniques, e.g., bromine number. Generally, the alpha-olefin will be present in stoichiometric excess of the amount theoretically required by can be substantially less than this. If desired, excess alpha-olefin can be separated from the metathesis product effluent and recycled to this stage.

Employing known apparatus and procedures, the effluent from the olefin metathesis operation is separated into a light fraction predominantly made up of $C_{3-8}$ hydrocarbons and a heavy fraction largely made up of $C_9+$ hydrocarbons. If desired, the heavy fraction can be further resolved into a $C_9$-$C_{18}$ fraction and a fraction containing the $C_{19}+$ hydrocarbons. The $C_{3-8}$ fraction and the $C_{19}+$ fraction, if there is one, are then recycled to the olefin oligomerization stage. At least part of the recycled lighter alpha olefins will undergo chain growth to heavier products including those within the desired range of carbon content. Conversely, at least a part of the recycled $C_{19}+$ alpha olefins will undergo cracking to lighter products including those within the desired range of carbon content.

GENERAL PROCESS DESCRIPTION

A $C_{3-7}$ olefinic feedstock, e.g., propylene together with recycled light (and optionally, higher) alpha-olefins through line 32 is introduced through line 10, usually in the liquid state, and preheated to reaction temperature by passing sequentially through a series of heat exchange means 11, 12 and 13 prior to entering the first of three serially connected adiabatic fixed bed olefin oligomerization reactor units 14, 15 and 16 packed with HZSM-5 catalyst. Advantageously, the maximum temperature differential across only one reactor is about 30° C. (ΔT about 50° F.) and the space velocity (LHSV based on olefin feed) is about 0.1 to 1, preferably about 0.5. While process pressure may be maintained over a wide range, usually from about 2800 to over 20,000 kPa (400–3000 psia), the preferred pressure is about 7000 to 15,000 kPa (1000 to 2000 psia). Inter-unit cooling of the heavier olefin-containing effluent from 14 to prevent excessive temperatures (normally 200°–300° C.) is achieved in heat exchange means 13. The effluent from oligomerization unit 15 is cooled in similar heat exchange means 12 and the effluent from oligomerization unit 16 is cooled in heat exchange means 11.

In a typical continuous process run under steady state conditions using HZSM-5 catalyst, the average reactor temperature in the series of adiabatic fixed bed reactor is maintained below about 260° C. (500° F.). In order to optimize formation of higher molecular weight hydrocarbons, effluent temperature from the terminal reactor 16 is kept substantially below about 290° C. (550° F.). Catalyst in the terminal position is preferably the most active in the series, being fresh or regenerated to maintain a high alpha value. By controlling the moderate reaction temperature, especially in the last bed, undesired cracking of the product hydrocarbons can be minimized.

Effluent from reactor unit 16 under process pressure and elevated temperature enters a first separator unit 17 wherein a fraction rich in $C_{3-30}$ olefins is recovered through line 21. The lighter overheads from separator 17 is passed to separator unit 18 with the light overheads being recovered through line 19 and the heavier bottoms being recovered through line 20 and combined with the olefins passing through line 21 into metathesis reactor unit 22. Make-up alpha-olefin, e.g., ethylene, is introduced through line 23 and with unreacted alpha-olefin recovered from separator unit 24 through line 25, is passed to metathesis reactor unit 22 as cofeed together with the heavy olefin stream in line 21. Alpha-olefin effluent from 22 containing unreacted light alpha-olefin feed is conveyed through line 26 to separator unit 24 where the light alpha-olefin is separated and recycled. The alpha-olefin effluent is then passed through line 27 to splitter unit 28, a light fraction rich in $C_{3-8}$ alpha-olefins being recovered through line 29 and a heavy fraction containing the balance of the alpha-olefin product and made up largely of $C_9+$ product is recovered through line 30. The $C_{3-8}$ product can be withdrawn through line 31 but at least a part, and preferably all, of the product is recycled through line 32 to the olefin oligomerization units. The $C_9+$ product is then separated in unit 33 into a lighter $C_{9-18}$ alpha-olefin fraction which is recovered through line 34 and a $C_{19}+$ olefin fraction which is recycled through line 35 to be combined with the $C_{3-8}$ fraction passing through line 32 to serve as cofeed for the oligomerization conversion carried out in reactors 14, 15 and 16.

What is claimed is:

1. A process for preparing alpla-olefins is provided which comprises:
    (a) converting a feed containing a mixture of lower alpha-olefin hydrocarbons in the presence of a medium pore crystalline silicate zeolite catalyst under reaction conditions providing a mixture of higher olefinic products including slightly branched higher olefininc products;
    (b) contacting at least a part of the slightly branched higher olefinic products resulting from step (a) with an alpha-olefin in the presence of a metathesis catalyst under olefin metathesis conditions to provide a mixture of slightly branched alpha-olefins having a different carbon number than the feed olefin;
    (c) separating the alpha-olefin product of step (b) into at least two fractions, one fraction containing predominantly lower alpha-olefin hydrocarbons and the other fraction containing predominantly slightly branched higher alpha-olefin hydrocarbons; and,
    (d) recycling at least a part of the lower alpha-olefin hydrocarbon fraction resulting from step (c) as feed for step (a).

2. The process of claim 1 wherein the catalyst of step (a) is HZSM-5.

3. The process of claim 1 wherein step (a) is carried out in a series of reactors.

4. The process of claim 1 wherein the ratio of intracrystalline acid sites to surface active sites in the catalyst of step (a) is increased prior to utilization of the catalyst.

5. The process of claim 2 wherein the ratio of intracrystalline acid sites to surface active sites of HZSM-5 is increased prior to utilization of the catalyst.

6. The process of claim 1 wherein the metathesis catalyst of step (b) is a supported oxide of molybdenum, tungsten or rhenium.

7. The process of claim 6 wherein the catalyst of step (b) additionally contains a rare earth metal oxide.

8. The process of claim 1 wherein a stoichiometric excess of alpha-olefin is employed in step (b).

9. The process of claim 1 wherein the alpha-olefin in step (b) is ethylene.

10. The process of claim 1 wherein in step (c), the alpha-olefin product of step (b) is separated into a light alpha-olefin fraction and a heavy alpha-olefins fraction.

11. The process of claim 10 wherein the light fraction is predominantly made up of $C_{3-8}$ alpha-olefins and the heavy fraction is predominantly made up of $C_9+$ alpha-olefins.

12. The process of claim 1 wherein in step (c), the alpha-olefin product of step (b) is separated into a light, intermediate and heavy alpha-olefin fraction and the light and heavy alpha-olefin fractions are recycled to step (a).

13. The process of claim 12 wherein the light fraction is predominantly made up of $C_{3-8}$ alpha-olefins, the intermediate fraction is predominantly made up of $C_{9-18}$ alpha-olefins and the heavy fraction is predominantly made up of $C_{19}+$ alpha-olefins.

14. The process of claim 1 wherein the entire olefinic hydrocarbon effluent from step (a) is employed as feed for step (b).

15. The process of claim 1 wherein in step (d), the entire lower alpha-olefin hydrocarbon fraction resulting from step (c) is recycled as cofeed for step (a).

16. The process of claim 9 wherein, following step (b), unreacted ethylene is separated from the alpha-olefin product effluent, said ethylene being recycled as cofeed to step (b).

17. The process of claim 1 for continuously preparing alpha-olefins predominantly within the $C_9+$ range of carbon content.

18. The process of claim 1 for continuously preparing alpha-olefins predominantly within the $C_{9-18}$ range of carbon content.

* * * * *